United States Patent [19]

Baumgarten et al.

[11] Patent Number: 4,681,851

[45] Date of Patent: Jul. 21, 1987

[54] BIOLOGICALLY ACTIVE COMPOSITION FOR PURIFYING WASTE WATER AND OUTGOING AIR

[75] Inventors: Jörg Baumgarten; Werner Frommer, both of Wuppertal; Theo Mann, Langenfeld; Imre Pascik, Monheim; Hans-Georg Rast, Leichlingen; Dietmar Schäpel, Cologne, all of Fed. Rep. of Germany

[73] Assignee: Bayer Aktiengesellschaft, Leverkusen, Fed. Rep. of Germany

[21] Appl. No.: 910,056

[22] Filed: Sep. 22, 1986

Related U.S. Application Data

[60] Division of Ser. No. 764,688, Aug. 12, 1985, Pat. No. 4,634,672, which is a continuation of Ser. No. 594,876, Mar. 29, 1984, abandoned.

[30] Foreign Application Priority Data

Apr. 8, 1983 [DE] Fed. Rep. of Germany ....... 3312578

[51] Int. Cl.$^4$ .................... D06M 16/00; C12N 11/04; C07G 15/00; C02F 3/00
[52] U.S. Cl. .................................... 435/262; 210/601; 435/180; 435/182; 435/264; 435/268
[58] Field of Search ............... 435/262, 264, 268, 174, 435/176, 177, 180, 182; 210/601

[56] References Cited

U.S. PATENT DOCUMENTS

| | | | |
|---|---|---|---|
| 3,859,169 | 1/1975 | O'Driscoll et al. | 435/182 |
| 4,167,107 | 9/1979 | Simmonds | 72/239 |
| 4,177,107 | 12/1979 | Kumakurz et al. | 435/181 |
| 4,195,129 | 3/1980 | Fukui et al. | 435/182 |
| 4,226,938 | 10/1980 | Yoshida et al. | 435/176 |
| 4,272,617 | 6/1981 | Kzetsu et al. | 435/182 |
| 4,342,834 | 8/1984 | Wood et al. | 435/182 |
| 4,436,813 | 3/1984 | Wood et al. | 435/182 X |

FOREIGN PATENT DOCUMENTS

| | | | |
|---|---|---|---|
| 089165 | 3/1983 | European Pat. Off. | |
| 2929872 | 3/1981 | Fed. Rep. of Germany | |
| 2233334 | 10/1975 | France | |
| 132883 | 8/1982 | Japan | 435/182 |
| 1550465 | 8/1979 | United Kingdom | |

OTHER PUBLICATIONS

European Journal of Applied Microbiology and Biotechnology 7, pp. 351 et seq. (1979).
J. Klein and M. Kluge, Institute of Chemical Technology, TU Braunschweig, Biotechnical Letters, vol. 3, No. 2, 65–70 (1981).

*Primary Examiner*—David M. Naff
*Attorney, Agent, or Firm*—Gene Harsh; Joseph C. Gil

[57] ABSTRACT

Waste water and/or outgoing air are purified by contact with a polyurethane hydrogel containing surface active coal, a polymer having cationic groups and cells having enzymatic activity and being capable of growth.

7 Claims, No Drawings

BIOLOGICALLY ACTIVE COMPOSITION FOR PURIFYING WASTE WATER AND OUTGOING AIR

This application is a division of application Ser. No. 764,688 filed Aug. 12, 1985, now U.S. Pat. No. 4,634,672, which itself is a continuation of application Ser. No. 594,876, filed Mar. 29, 1984, now abandoned.

The present invention relates to biologically active compositions which are based on hydrogels containing finely divided surface active coal, polymers having cationic groups and micro-organism cells which are capable of growth and to a process for the production thereof by reacting isocyanate prepolymers with aqueous suspensions which contain surface active coal and polymers having cationic groups, the cells which are capable of growth being immobilized directly with the aqueous suspensions or being added in a second step to the hydrogel obtained in a first step.

BACKGROUND OF THE INVENTION

The combination of surface-active solid substances with microorganisms to increase the activity thereof in bio-conversion processes is known. By way of example, in accordance with FR-A No. 2,233,334, ion exchange resins are added to enzyme suspensions. The adsorption of cells on, for example, $Al_2O_3$, bentonites and $SiO_2$ and their subsequent embedding in polyacrylates is described in DE-A Nos. 2,633,259 and 2,703,834.

The embedding of cells in polyacrylates or polyurethane gels to improve the handling of the cells in bio-conversion processes is known. DE-A No. 2,629,692 describes the embedding in photohardenable resin, such as in polyurethane containing photocrosslinkable acrylate double bonds. Tanaka et al. describe, in the *European Journal of Applied Microbiology and Biotechnology* 7, Pates 351 et. seq. (1979), a process for embedding complete cells in polyurethane-hydrogel. The cells which are not capable of growth display, in an immobilized state, enzymatic activity in bio-conversion processes. The embedding of cells which are optionally capable of growth in polyurethane-hydrogels is described in DE-A No. 2,929,872.

The hitherto known combinations of surface-active substances and cells, which were optionally also embedded in gels, were not suitable for purifying waste water or outgoing air in a simple and effective manner.

SUMMARY OF THE INVENTION

It has now been found that the decomposition capacity of micro-organism cells which are immobilized in hydrogels for waste water and outgoing air treatment and the handling thereof in purification processes can be improved if the cells which are capable of growth are immobilized by polyurethane hydrogels which are obtained by reacting isocyanate prepolymers with water, in the presence of surface active coal and polymers having cationic groups.

DETAILED DESCRIPTION

The present invention thus relates to carrier materials which contain micro-organism cells having an enzymatic activity and are based on polyurethane hydrogel which contain surface active coal, polymers having cationic groups and cells having enzymatic activity which hydrogel is characterized in that the cells which are immobilized by polyurethane-hydrogel are cells which are capable of growth.

The present invention relates furthermore to a process for the production of biologically active compositions which comprise hydrogels which contain surface active coal, polymers having cationic groups and microorganism cells which are capable of growth; the process is characterized in that mixtures of finely divided coal and polymers which have cationic groups are gelled in polyurethane-hydrogels, cells capable of growth either being directly embedded in said hydrogels together with the other components or being added in a second step to the gel obtained. Optionally di- and-/or polyamines may be used in the production process but water is preferably used as the sole chain lengthening agent.

The micro-organism cells which are present in digested and activated sludge from sewage purification plants and/or cells which are capable of growth and are adapted for the metabolization of specific substances may be used as the cells inserted into the carrier materials according to the present invention. The cells which are capable of growth and are adapted for the metabolization of specific substances are conventional activated sludge organisms which are specifically adapated for increasing activity. Microorganisms of this type are known and described, for example, in Appl. Environ Microbiol., Vol. 42, p. 44-55 (1981), DE-A Nos. 3,046,686 or 3,225,885.

The micro-organism cell content, based on dry matter, in the compositions according to the present invention is from 0.3 to 10, eventually up to 15%, by weight, preferably from 0.5 to 10%, by weight, and most preferably from 0.8 to 5%, by weight, based on the total weight of the reaction mixture for the preparation of the composition.

By way of example, standard ion exchange resins which have cationic groups or other polymers which have structures containing positively-charged nitrogen atoms may be included according to the present invention as polymers which have cationic groups, such as for example: polyaminocarboxylic acid esters having cationic groups, polyacrylamides having cationic groups, polyethylene imines having cationic groups, copolymers of acrylonitrile, styrene and dimethylaminoethyl methacrylate having cationic groups, condensation products of diethylene triamine and maleic anhydride having cationic groups, copolymers of isobutylene and maleic anhydride, followed by imidization with specific diamines, having cationic groups. These substances are embedded in the form of aqueous dispersions in the compositions according to the invention. The content of polymers having cationic groups in the compositions according to the invention is 0.2–20% by weight, preferably 0.5–15% by weight, and most preferably 1–10% by weight, based on the total weight of the reaction mixture for the preparation of the composition.

According to the invention finely divided surface active coal is understood as meaning pulverized charcoal (active carbon) or similiar materials resp. intermediate products which already reveal properties characteristic for active carbon, such as large specific surface, porosity, and the formation of surface electrical charge.

Such substances e.g. are pyrolytically treated natural coal, pyrolyzed bone meal, or carbon black. An essential requirement for such materials is a specific surface according to BET of above 50, preferably above 100 $m^2/g$.

Types of active carbon which may be used according to the present invention are those which are obtained in large-scale production processes, and in addition those which have been neutralized by suitable additives and which have also been optionally subjected to a so-called ash removal operation.

The types of surface active coal can be used individually or in mixtures. The grain size of the types of surface active coal may be from 0.5 to 1000 $\mu$m. The content of these substances is from 0.5 to 40%, by weight, preferably from 0.5 to 30%, by weight, and most preferably from 1 to 20%, by weight, based on the total weight of the reaction mixture.

The covalently cross-linked polyurethane-hydrogels which are contained in the carrier materials according to the present invention may be obtained by reacting NCO-prepolymers or -semiprepolymers with water in which di- or polyamines are optionally contained as chain lengthening agents or as cross-linked agents. Gels of this type are described for example in DE-A No. 2,347,299 and in DE-A No. 2,521,277. The prepolymers and semiprepolymers have isocyanate end groups and are produced in a known manner by reacting polyethers which contain at least 30%, by weight, of $-\!\!\!-\!\![CH_2.CH_2.O]\!-\!\!\!-$ units ("ethylene oxide units") with an excess quantity of di- and/or polyisocyanate. During the course of this reaction the quantity of di- and/or polyisocyanate is preferably calculated in such a way that the NCO/OH ratio, which is dependent on the desired qualities of the type of prepolymer to be produced, is from 2 to 10. The isocyanate group content of the prepolymer or semiprepolymer is advantageously from 1 to 15%, by weight, preferably from 2 to 10%, by weight, and most preferably from 2,5 to 4,5%, by weight, based on the weight of the prepolymer or semiprepolymer.

Isocyanate prepolymers which are released to such an extent from monomeric di- or polyisocyanates by suitable production steps, such as thin layer distillation, that the monomeric content thereof is below 1%, by weight, preferably below 0.5%, by weight, are particularly preferred according to the present invention, the isocyanate content being 1.5 to 4% by weight based on the prepolymer which has been subjected to thin layer distillation. Prefered isocyanate prepolymers are those on basis toluylendiisocyanats.

The starting materials for the NCO-prepolymers or semiprepolymers are polyoxyalkylene ethers which have a molecular weight of from 500 to 10,000, preferably from 2,000 to 8,000 and have at least two active hydrogen atoms and which contain at least 30%, by weight of ethylene oxide groups in the form of oxyethylene groups —O.CH$_2$. CH$_2$—, based on the weight of the polyether, in addition to preferably oxypropylene groups. Polyethers of this type are produced by reacting compounds which have reactive hydrogen atoms, such as di- or polyalcohols, di- or polyphenols, aliphatic or aromatic di- or polyamines, with ethylene oxide and optionally alkylene oxides, such as propylene oxide, butylene oxide, styrene oxide, epichlorohydrin or mixtures of these alkylene oxides.

More than difunctional polyethers, such as at least trifunctional ethers, are preferred since they produce covalently cross-linked gels.

Further starting compounds for the NCO-prepolymers or semiprepolymers are aliphatic, cycloaliphatic, araliphatic, aromatic or heterocyclic polyisocyanates, such as are described by W. Siefken, *Liebigs Annalen der Chemie,* Vol. 562, pages 75–136.

By the way of example, the polyisocyanates which are described in DE-A Nos. 2,347,299 and 2,521,277 may be included as polyisocyanates. The following are examples thereof: toluylene diisocyanates, the diphenylmethanediisocyanates in the form of the 4,4'- and/or 2,4'- and/or 2,2'-isomers thereof, also mixtures of the diphenylmethanediisocyanates with the tri and higher-nuclear homologs and isomers thereof. The conventional modification products of said toluylene or diphenylmethane-di- and -poly-isocyanates by allophanatization, biuretization, dimerization, trimerization, carbodiimidization or reaction with stoichiometrically deficient quantities of di- and/or polyfunctional compounds such as water or di- or polyols are also suitable.

Toluylene diisocyanates are most particularly preferred as 2,4- or 2,6- isomers or the isomeric mixtures thereof. Aliphatic or cycloaliphatic di- and polyisocyanates may be used, such as hexamethylene 1,6-diisocyanates, isophoronediisocyanate, biuretisized hexamethylene diisocyanate or dicyclohexylmethane diisocyanates in the position and/or stereoisomers thereof or the mixtures thereof.

The quantity of NCO-prepolymers, which are used in the production of the composition according to the present invention (corresponding to the polyurethane solid substance) is from 5 to 30%, by weight, preferably from 10 to 25%, by weight, and most preferably from 15 to 20%, by weight, based on the total weight of the reaction mixture for the production of the composition.

The water which is simultaneously used in the production of the composition according to the present invention is, in addition to being a dispersion agent for the cells and the other substances and for the prepolymers or semiprepolymers also important as a reaction component for the prepolymers which have isocyanate groups. The water content is from 20 to 90%, by weight, preferably from 40 to 85%, by weight, and most preferably from 50 to 85%, by weight, based on the total weight of the reaction mixture during the production of the composition.

Di- and/or polyamines may optionally be simultaneously used as low molecular weight chain lengthening agents or as cross-linking agents. The following are examples of aliphatic, cycloaliphatic or aromatic di- or polyamines of this type: ethylene diamine, hexamethylene diamine, diethylene triamine, hydrazine, guanidine carbonate, N,N'-diisopropylhexamethylene diamine, 1,3-bis-aminomethyl-benzene, N,N'-bis-(3-aminopropyl)-ethylene diamine, N,N'-bis-(2-aminopropyl)ethylene diamine, N,N'-(2-aminoethyl)-ethylene diamine, 4,4'-diamino-diphenyl methane, 4,4'-dimethylamino-3,3'-dimethyl-diphenyl methane, 2,4'-diamino-diphenyl methane and 2,4- or 2,6-diaminotoluene.

The di- or polyamine content is from 0.2 to 5%, preferably from 1 to 4%, based on the total weight of the reaction mixture for the production of the composition.

The following are examples of additives which may be added to the carrier materials according to the present invention: density-increasing substances such as barite, metal powder, powdered rubber, clay powder, pumice powder, glass powder, powder obtained from the kernels and shells of olives and nuts, rock-flour; density-reducing substances such as small polystyrene globules, wood powder, powder from plastic waste, hollow microbeads, polyethylene foam flakes; colouring agents such as colouring pigments, dyes; short fibres of an organic or inorganic base such as glass fibres and gel-forming macromolecular substances such as types of cellulose, alginates, starch, carrageenans.

The biologically active compositions according to the invention may be produced in various ways. All the components, i.e., gel-forming agents, polymers having cationic groups, surface active coal, water and cells may, for example, be added at once and intensively mixed. The components may also be added one after the other. In the multistep method, the NCO-prepolymer or semi prepolymer is firstly mixed with some of the water; then the cells which are suspended with the remaining water are stirred into this mixture. According to one commercially particularly advantageous embodiment of this multistep process, the gel-forming substance is firstly intensively mixed with water and the cell suspension is subsequently added. A further multistep method of procedure preferred according to the invention comprises first mixing together finely divided coal and polymers having cationic groups and prepolymers in water and converting the mixture into a gel. Then, in further process steps, the resulting gel is mixed in the form of small particles with dispersion or suspensions containing cells capable of growth, for 1 to 50 hours, and then the resulting biologically active composition is separated from excess suspension or dispersion.

In these methods, the transport, dosing and mixing of the individual component mixtures may be carried out in apparatus which are known to those skilled in the art. It is possible to transport and dosing the cell suspension, for example, with a suitable screw. The subsequent addition of the cell suspension to the reactive, gel-forming mixture is carried out, for example, in a mixing head which is equipped with a stirrer or in a static mixer. Air or nitrogen may be added to the gel-form reaction mixture in order to obtain a foam-like gel mass. A foam gel can also be obtained by other steps, such as for example by increasing the temperature of the water component or by increasing the concentration of the prepolymer component.

The foamed gel mass can be produced with complete open cells by adding cell opening agents to the reaction mixture. Such agents are highly ethylene oxide containing polyethers with at least trifunctional starter molecules. The content of cell opening agents is from 1 to 15%, by weight, based on the total weight of the reaction mixture for the production of the composition.

The production of the compositions according to the present invention may be carried out continuously or discontinuously. The method depends on the form which the materials according to the present invention are to have. If blocks or rods are to be produced which will be subsequently cut into thin sheets, the discontinuous method is preferably carried out. If the compositions according to the present invention are to be produced, however, in this pieces having suitable dimensions, then the continuous method is more advantageous. In this case, a continuous stripshaped produced is first of all produced which is subsequently cut into individual pieces, such as plates or films or small particles. In this procedural method, the reactive gel mixture containing cells may also be sprayed or doctored before it solidifies due to the reaction. For this purpose the reactive mixture may be applied to the most varied materials based on natural or synthetic raw materials, such as to films, mats, fleeces, worked cloth, knitted cloth, woven cloth or foam films.

The compositions according to the present invention may be used in the most varied forms, such as granulated material, plates, films, blocks or strips. The compositions are used according to the conventional procedural methods of waste water technology, under aerobic or anaerobic conditions.

One advantage of the compositions according to the present invention as opposed to the gel-shaped or foamed bio-catalysts, based on polyurethane and containing complete cells which are known from German Offenlegungsschrift No. 2,929,872 lies in the improved decomposition capacity of industrial waste waters which are charged with organic compounds. The improved effectiveness of the compositions according to the present invention is particularly evident in industrial waste water which contain nitro, chloro- and amino-substituted aromatic compounds.

A further advantage of the new compositions is that even sensitive complete cells may be embedded in them, if isocyanate prepolymers which have a low content of reactive isocyanate groups are also used as gel-forming agents. The growth capacity of complete cells which are sensitive with respect to reactive isocyanates is maintained in this manner.

The following Examples explain in more detail the present invention. The parts which are given in the Examples are parts, by weight, unless otherwise specified.

EXAMPLE 1

(a) The Production of the Biologically Active Composition 7 parts of an aqueous suspension (biological damp mass), which contains 15%, by weight, of specifically cultured cells according to German Pat. No. 3,225,885, Example 1, were stirred into 67.5 parts of water which has been adjusted to pH 7 with phosphate buffer. Over a period of 30 seconds, 7.5 parts of neutral finely-powdered active carbon and 1 part of ion exchange resin which has cationic groups and is in powder form (type: Lewasorb A 50, Bayer AG) and then 17 parts of isocyanate-prepolymer A, the production of which is described in the following, were successively added thereto with intensive stirring. Gelatification occurs after a further 45 seconds of stirring. An elastic gel mass was obtainned which was subsequently crushed to produce particles which have an average diameter of from 2 to 3 mm.

The isocyanate prepolymer A which was used was obtained as follows:

A mixture consisting of 159 parts of toluylenediisocyanate (80% of 2,4- and 20% of 2,6-isomers) and 1,200 parts of a trifunctional polyether which has been obtained by adding 60%, by weight, of ethylene oxide and 40%, by weight, of propylene oxide to glycerine and which has a hydroxyl number of 28, is heated to 80° C. with stirring over a period of 30 minutes. At this temperature the reaction mixture is stirred for a further 3 hours and is then cooled to room temperature. The prepolymer which is obtained has an isocyanate content of 3.7% and a viscosity of 9,500 mPa.s at 25° C.

(b) The Purification of Waste Water with the Biologically Active Compositions Waste water which also contains nitro-, chloro-and amino-substituted aromatic compounds in a concentration of up to 200 ppm in addition to naphthalene sulphonic acids as an organic compound is treated with the compositions which are obtained according to Example 1(a). The waste water is changed daily. After the experiment has been continued for 1 month, the decomposition capacity of the biologically active composition is 98% of the organic carbon (TOC).

EXAMPLE 2

The biologically active composition was produced according to the method of Example 1. 2 parts of a 26%, by weight, aqueous solution of a polyelectrolyte based oh a polyamino carboxylic acid ester having cationic groups (type: Praestol 185 K manufactured by the Stockhausen company) were used instead of 1 part of ion exchanger powder.

The decomposition capacity of the composition was examined according to the method of Example 1 and using the type of waste water which is described in the method in Example 1. After the experiment has been likewise continued for one month, the composition achieved a decomposition of 92% of the organic carbon.

EXAMPLE 3

(a) Preparation of the Biologically Active Composition 10 parts of neutral finely pulverized active carbon (type: Carboraffin AP, manufactured by the Bayer company) and 2 parts of pulverized ion exchange resin based on polystyrene and having cationic groups (type: Lewasorb A 50, manufactured by the Bayer AG company) and 7 parts of a polyether which had been obtained by adding 70%, by weight, of ethylene oxide and 30%, by weight, of propylene oxide to trimethylolpropane and which had a hydroxyl number of 56, were dispersed in 59 parts of water and then 22 parts of the isocyanate prepolymer described in Example 1 were added and stirred, with the introduction of nitrogen. 110 seconds after the prepolymer had been added the gel formation occurred. A foamed elastic gel mass was obtained which was comminuted into particles having a diameter of 3–4 millimeters.

500 millimeters of waste water from the chlorine bleaching installation of a pulp mill (TOC content: 900 ppm), 30 millimeters of digested sludge (content of dry substance: 20 parts per liter) from the digestion tower of a minicipal sewage treatment plant and 30 parts of the above-mentioned gel particles were fed into a 1 liter vessel having a stirring device and an inlet and outlet as well as a gas measuring device and stirred for 24 hours at a temperature of 35° C. with the exclusion of oxygen. Then the excess digested sludge was rinsed out with waste water with nitrogen-fumigation. Gel particles were obtained which contained microorganisms capable of growth.

(b) Purification of the Waste Water with the Biologically Active Composition 30 parts of the biologically active carrier material obtained according to Example 3a were introduced into a vessel as described in Example 3a and 500 milliliters of waste water from the chlorine bleaching installation of a pulp mill were added. The waste water had a content of 900 ppm of organic carbon (TOC). The mixture of waste water and carrier material was stirred at 50 revolutions per minute with the exclusion of oxygen. During the period over which the test was carried out 50 milliliters of the treated waste water were removed each day and replaced by 50 milliliters of fresh waste water. The following values were obtained 3 weeks after the beginning of the test: 366 ppm of organic carbon (TOC) in the treated waste water. Biogas production ($CH_4 + CO_2$): 67 milliliters per day.

EXAMPLE 4

(a) Preparation of the Biologically Active Composition 14 parts of neutral, finely pulverized active carbon (type: Carboraffin AP, manufactured by the Bayer AG company) and 4 parts of a polyamino carboxylic acid ester having cationic groups (type: Praestol 185 K, manufactured by the Stockhausen company) were dispersed in 152 parts of water. Then 30 parts of the isocyanate prepolymer described under Example 1 were mixed therewith. Gel formation occcurred after 90 seconds. The gel mass obtained was comminuted into particles having a diamter of 2–3 millimeters. 160 parts of these particles were introduced into an up-flow reactor of a capacity of 1.6 liters and 120 milliliters of digested sludge (content of dry substance: 7.6 parts per liter) from the digestion tower of a municipal sewage treatment plant as well as 1 liter of evaporator condensate. The evaporator condensate, which had been obtained during the evaporation of the sulfite liquor in the manufacture of pulp, had a COD content of 44,000 ppm and was diluted with water to 4,900 ppm. After stirring for 24 hours at a temperature of 35° C. with the exclusion of air biologically active carrier material was obtained.

(b) Purification of Waste Water 160 parts of the carrier material obtained in Example 4a were introduced into a 1.6 liter up-flow reactor and the evaporator condensate described in Example 4a was continuously introduced and discharged with the aid of a metering pump and under anaerobic conditions the quantity of waste water passing through the reactor being 640 milliliters per day. After 43 days of continuous operation the following value was found in the outflowing waste water:

COD value: 3650 ppm

EXAMPLE 5

(a) Preparation of the Biologically Active Composition 15 parts of neutral, finely pulverized active carbon (type: Carboraffin AP, manufactured by Bayer AG company) and 4 parts of pulverized ion exchange resin based on polystyrene and having cationic groups (type: Lewasorb A 50, manufactured by the Bayer AG company) were dispersed in 131 parts of an activated sludge suspension (content of dry substance: 2 parts per liter) which had been taken from the clarification installation of a carbonizing plant. 50 parts of the isocyanate prepolymer B described below were added to this suspension and intensively mixed therewith. 2 minutes after the addition of the prepolymer a gel formed. The gel mass was comminuted into particles having a diameter of 2–4 millimeters.

The prepolymer B used was obtained as follows:

A mixture of 213 parts of toluylene diisocyanate (80% of the 2,4-isomer and 20% of the 2,6-isomer) and 1587 parts of a polyether which had been obtained by the addition of 60% by weight of ethylene oxide and 40% by weight of propylene oxide to glycerol and has a hydroxyl number of 28 was heated with stirring to 80° C. over a period of 30 minutes. The reaction mixture was stirred at this temperature for a further 5 hours.

Then excess monomeric toluylene diisocyanate was distilled off. The prepolymer obtained had an isocyanate content of 1.9% and a viscosity of 12960 mPas at 25° C.

(b) Purification of Waste Water 150 parts of the carrier material prepared according to Example 5a were introduced into a 3 liter OECD laboratory-scale waste water treatment device which was equipped with an inlet and an outlet and aeration and settling devices and waste water from a carbonizing plant which had been diluted with water and then had a COD content of 961 ppm and a content of phenols of 293 ppm, was introduced and discharged continuously under aerobic conditions. The quantity of waste water passed through the device each day was 5.8 liters. After the device had been operated for 4 days the following values were measured in the outflowing waste water: COD content: 365 ppm, content of phenols 162 ppm.

EXAMPLE 6

(a) Preparation of the Biologically Active Composition 900 parts of neutral finely pulverized active carbon (type: Carboraffin AP, manufactured by the Bayer AG company) and 200 parts of ion exchange resin based on polystyrene and having cationic groups (type: Lewasorb A 50 manufactured by the Bayer AG company) were dispersed in 7400 parts of water. This dispersion was continuously mixed with the isocyanate prepolymer C described below, in a ratio of 5 parts of dispersion to 1 part of prepolymer C. The liquid reaction mixture was introduced was filled into boxes each 1 meter times 0.2 meters in size and to a height in each box of 3 centimeters. After 3 minutes an elastic gel mass was obtained which was then comminuted into particles of a diameter of 3 to 5 millimeters. 3600 parts of these particles were introduced into an up flow reactor having a capacity of 33 liters and 2 liters of digested sludge (content of dry substance: 40 parts per liter) from the anaerobic waste water treatment plant of a sugar refinery and 25 liters of waste water from the mechanical preclarification tank of a municipal waste water treatment plant were added. After agitation with nitrogen bubbles for 12 hours at a temperature of 35° C. biologically active carrier material was obtained.

The prepolymer C used had been obtained as follows: 865 parts of a polyether which has been obtained by the addition of 60% by weight of ethylene oxide and 40% by weight of propylene oxide to glycerol and has a hydroxyl number of 28, are mixed homogeneously with 135 parts of 1,6-hexamethylene diisocyanate and the mixture is heated to 105° C. The reaction mixture is stirred at this temperature for 7 hours then cooled to room temperature. Then 0.1% by weight of benzoyl chloride is added and the mixture stirred until homogeneous. The prepolymer obtained has a content of isocyanate groups of 5.1% by weight and a viscosity (at 23° C.) of 7400 mPas.

(b) Purification of Waste Water

The carrier material produced according to Example 6a was used in the following way in the up-flow reactor (33 liter capacity) for purifying waste water under continuous and anaerobic conditions. 70 liters of mechanically preclarified waste water from a municipal sewage treatment plant having a COD content of 266 ppm and a TOC content of 62 ppm were passed through the reactor per day. After 6 days of continuous operation a COD content of 44 ppm and TOC content of 15 ppm were measured in the outflowing water.

We claim:

1. In a process for the biological purification of waste water and/or outgoing air, by contacting said air and/or water with a biological composition, the improvement wherein said biological composition is a biologically active composition comprising a polyurethane hydrogel containing (i) surface active coal having a specific surface according to BET of above 50 $m^2/g$, (ii) a polymer having cationic groups, and (iii) cells having enzymatic activity and being capable of growth.

2. The process of claim 1 wherein said polymer (ii) is an ion exchange resin.

3. The process of claim 1 wherein said polymer (ii) is a polymer which contains positively-charged nitorgen atoms.

4. The process of claim 1 wherein said cells (iii) occur in the digested and activated sludge of clarification plants.

5. The process of claim 1 wherein said cells (iii) are adapted for the metabolization of specific substances.

6. The process of claim 1 wherein said hydrogel is prepared from a toluene diisocyanate prepolymer having an isocyanate group content of from 1.5 to 4% by weight and having a free toluene diisocyanate content of less than 1% by weight, and water.

7. The process of claim 1 wherein said coal (i) is present in an amount of from 0.5 to 40% by weight, said polymer (ii) is present in an amount of from 0.2 to 20% by weight, and said cells (iii) are present in an amount of from 0.3 to 15% by weight.

* * * * *